United States Patent [19]

Copley et al.

[11] Patent Number: 4,870,244
[45] Date of Patent: Sep. 26, 1989

[54] METHOD AND DEVICE FOR STAND-OFF LASER DRILLING AND CUTTING

[76] Inventors: John A. Copley, Rte. 11, Box 1022, Fredericksburg, Va. 22405; Hoi S. Kwok; Yacov Domankevitz, both of 214 Bonner Hall, SUNY-Buffalo, Buffalo, N.Y. 14260

[21] Appl. No.: 254,629
[22] Filed: Oct. 7, 1988
[51] Int. Cl.$^4$ .................................................. B23K 26/00
[52] U.S. Cl. .............................. 219/121.7; 219/121.67; 219/121.65; 219/121.61
[58] Field of Search ........... 219/121.7, 121.71, 121.67, 219/121.72, 121.65, 121.66, 121.61, 121.62

[56] References Cited

U.S. PATENT DOCUMENTS

| | | | |
|---|---|---|---|
| 3,577,174 | 5/1971 | Longsderff | 372/82 X |
| 4,220,842 | 9/1980 | Sturmer et al. | 219/121.6 |
| 4,380,946 | 4/1983 | Dyson | 219/121.67 |
| 4,458,134 | 7/1984 | Ogle | 219/121.7 |
| 4,564,736 | 1/1986 | Jones et al. | 219/121.6 |
| 4,573,465 | 3/1986 | Sugiyama et al. | 219/121.76 X |
| 4,738,503 | 4/1988 | Desurvire et al. | 350/96.15 |
| 4,789,770 | 12/1988 | Kasner et al. | 219/121.74 X |

*Primary Examiner*—C. L. Albritton
*Attorney, Agent, or Firm*—John D. Lewis; Kenneth E. Walden

[57] ABSTRACT

A device for perforating material and a method of stand-off drilling using a laser. In its basic form a free-running laser beam creates a melt on the target and then a Q-switched short duration pulse is used to remove the material through the creation of a laser detonation wave. The advantage is a drilling/cutting method capable of working a target at lengthy stand-off distance. The device may employ 2 lasers or a single one operated in a free-running/Q-switched dual mode.

13 Claims, 2 Drawing Sheets

METHOD AND DEVICE FOR STAND-OFF LASER DRILLING AND CUTTING

BACKGROUND OF THE INVENTION

The invention described herein may be manufactured and used by or for the United States Government for governmental purposes without the payment of royalties thereon.

This invention relates to a device and method of laser drilling and cutting. More particularly, to a laser device using both a Q-switch and essentially continuous-wave output to cut or drill metal. A salient utility constituting a major advancement in the art is the ability to perform cutting or drilling operations on high conductivity metal targets at a stand-off distance of several meters.

Various types of laser devices have been developed in the past for the purpose of drilling, cutting, or otherwise removing material from a target. For example, U.S. Pat. No. 4,380,694 to Dyson discloses a laser cutting apparatus using a high power laser, particularly a $CO_2$ laser for cutting steel and other high conductivity metal targets. U.S. Pat. No. 4,220,842 to Sturmer also teaches a laser cutting device for metallic targets. This reference uses high power to create a laser supported detonation (LSD) wave to remove melted material from the workpiece. Another laser device for cutting and/or removing metal from a target is disclosed in U.S. Pat. No. 4,458,134 to Ogle. Therein a laser, preferably a Nd:YAG lases material from a metal workpiece. The workpiece sits atop a paper layer that creates a jet upon being hit by the laser beam as the beam perforates the workpiece. The jet blows the slag away from the workpiece keeping the workpiece free of deposits. Other methods known in the art to remove melted mterial from a target include various devices employing gas to blow the material away or oxygen to assist cutting. U.S. Pat. to Jones, No. 4,564,736 teaches a hand-held laser tool with an inert gas capability for welding and an oxygen supply for cutting. As a matter of fact, most laser cutting applications now employ gas assist to increase the efficiency and quality of the cutting process.

Obviously, heavy metal targets are difficult to cut using a laser device and require high power, gas assist or other methods to remove the melted material from a workpiece. This limitation manifests in one form as a limit on the distance the target can be located from the laser head. Gas assist can only be employed on close targets that the gas jet can reach and lasers employing high enough power to create a melt at distance suffer from an inability to remove the molten material from the workpiece. It therefore would be a marked advance in the art to be able to lase holes or cut metallic targets, e.g. 0.032 inch aluminum, at stand-off distances greater than a meter.

It is also desirable to drill holes with a minimal amount of energy as this reduces system weight especially in applications where gas assist cannot be employed due to separation of the target from the laser head or final focusing optics. Attempts using multiple pulses to first create a melt on the target and then to remove the molten material was discussed in an article authored by N. Rykalin, A. Uglov and A. Kokora, entitled Laser Machining and Welding. (M.I.R. Publishers, Moscow, 1978). Other attempts to reduce the power necessary for stand-off drilling of heavy metal targets have explored the use of a continuous-wave $CO_2$ laser and a Nd:YAG laser used together. The continuous-wave laser radiation preheats the material to temperatures near the melting point and the superimposed short Nd:YAG laser pulse provides the mechanical impulse from a laser supported detonation wave to remove the molten material.

The above discussed methods of enhancing laser drilling efficiency are based on the fact that the strength of most materials drops when the melting temperature is approached. Therefore, a mechanical shear or compressive impulse will be adequate to remove the material and create a hole or cut. Those skilled in the art will find it intuitively obvious than an energy saving equal to the latent heat of fusion and vaporization compared to thermal material removal can be realized.

Some disadvantages of the above discussed methods are heavy equipment, short target focusing distances and, on the two-laser devices known in the art, power supply and capacitor banks. It would, therefore, constitute a major advance in the art to increase drilling efficiency without adding system weight and still have a stand-off cutting and drilling capability.

None of the aforediscussed references whether taken alone or in any combination remotely suggest an improved laser drilling and cutting device as taught herein, employing a single laser operated first in a free-running mode and then Q-switched for a high energy pulse or two lasers operated in like manner sharing a single power supply. This power supply may be any commercially available pulsed power supply containing a capacitor bank for Q-switching excitation, such as that employed by Applicants in one embodiment reduced to practice; namely, a Holobeam Laser, Inc., Model 600 available from Orlando, Florida.

There is a plethora of utilities for a laser cutting device that is lightweight and field portable. The ability to process a workpiece at a stand-off distance measured in meters expands the effectiveness of assembly line robotics. One embodiment of the teachings of this invention is a field-portable stand-off device to disable ordnance by cutting the ordnance, or its wires or fuses, from a distance. By choosing a Nd:YAG laser an embodiment of this invention might cut or drill a distant target through a closed window or glass enclosure allowing personnel to perform such tasks on items without requiring physical access to them.

SUMMARY OF THE INVENTION

A special purpose advantage to the disclosed method of laser drilling and machining is the ability to work material in a vacuum without heavy auxillary equipment and heavy power supplies. This engenders many utilities and possibilities in our space programs.

OBJECTS OF THE INVENTION

An object of the invention is to provide a device and method of laser drilling and cutting that has an increased efficiency.

Another object of the present invention is to provide a laser cutting or drilling device that outputs both a free-running and Q-switched energy beam.

A further object of the instant invention is to provide a laser cutting and drilling device comprising readily available commercial parts.

Still another object of the invention is to provide a method of laser cutting and drilling of highly conductive metal workpieces without gas assist.

Another object of this disclosure is to teach a high efficiency laser cutting and drilling device that may function with various type lasers including those in the crystal laser class.

Yet another object of the present invention is to teach a laser cutting and drilling device that can output both a Q-switched and essentially C-W free running pulse with a single power supply which includes capacitor bank.

An additional object of the present invention is a device that is lightweight and field-portable.

A further object of one embodiment of the instant invention is a laser drilling and cutting device that provides an output of free-running laser engergy followed by a Q-switched high energy pulse from a single laser head.

Still yet another object of this disclosure is to present a lightweight, field portable, laser drilling and machining device that functions well in a vacuum and may be deployed in space without burdensome auxiliary equipment.

Another object of one embodiment of this invention is to provide a laser cutting and drilling device that can function on a workpiece separated from the device by a window pane.

Another object of the present invention is to teach a laser cutting and drilling device that can remove material from a heavy metal workpiece that is separated in distance from the device by several meters.

Still another object is to disclose a laser cutting and drilling device that can be taken into the field by explosive ordnance personnel and used to destroy or deactivate ordnance without the personnel being in close proximity to the target ordnance.

Another object of the present invention is to teach a device that is field portable while maintaining power and efficiency levels adequate to cut heavy ferrous metal targets.

In obtaining these and other objects, the invention provides a device that outputs both a Q-switched high energy pulse and an essentially C-W free-running pulse from a system having one or two laser cavities, but a single power supply and capacitor bank. This increases cutting and drilling efficiencies, reduces system weight and allows the target distance to be greatly increased from the laser head.

The foregoing and other objects and advantages of the invention will be further understood from the following detailed description of preferred methods and systems and from the drawings wherein like reference numerals identify like parts throughout.

DESCRIPTION OF THE DRAWINGS

Referring to FIG. 1, the numerical 30 designates a block diagram of the stand-off laser drilling and cutting device of the present invention using* dual power supplies. Therein a laser cavity 10, a rear cavity reflector 7 and a front partial cavity reflector B, provide a relatively long essentially continuous-wave free-running pulse output beam 18. Beam 18 is reflected off the alignment mirrors 14 and 15 and then focused through the focusing optics 20 onto the target 21. The laser employed in the test model illustrated in FIG. 1 is a Nd:YAG laser commercially available from Kigre, Inc. in Hilton Head, SC. The choice of an Nd:YAG laser, that produces an output unaffected by clear glass, allows target 21 to be separated from the focusing optics 20 by a pane of glass such as a window pane. FIG. 1 shows in phantom a possible window pane designated 22.

It should be understood that while the output of an Nd:YAG laser may pass unaffected through glass and therefore provides a capability to work a target separated from system 30 by a pane of glass such as a window, the choice of lasers is not restricted to a specific output wavelength laser. The techniques and system arrangement is applicable to any combination of pulsed lasers. The target characteristics, i.e., the coefficient of coupling to various laser wavelengths will allow one skilled in the art to choose the proper laser. The Nd:YAG lasers illustrated were selected for metal targets such as aluminum, steel, copper, and stainless steel. Should the target workpiece be plastic, glass, paper, or human tissue, a different type laser with an output having a wavelength easily absorbed by the target would be chosen.

Figure 1:
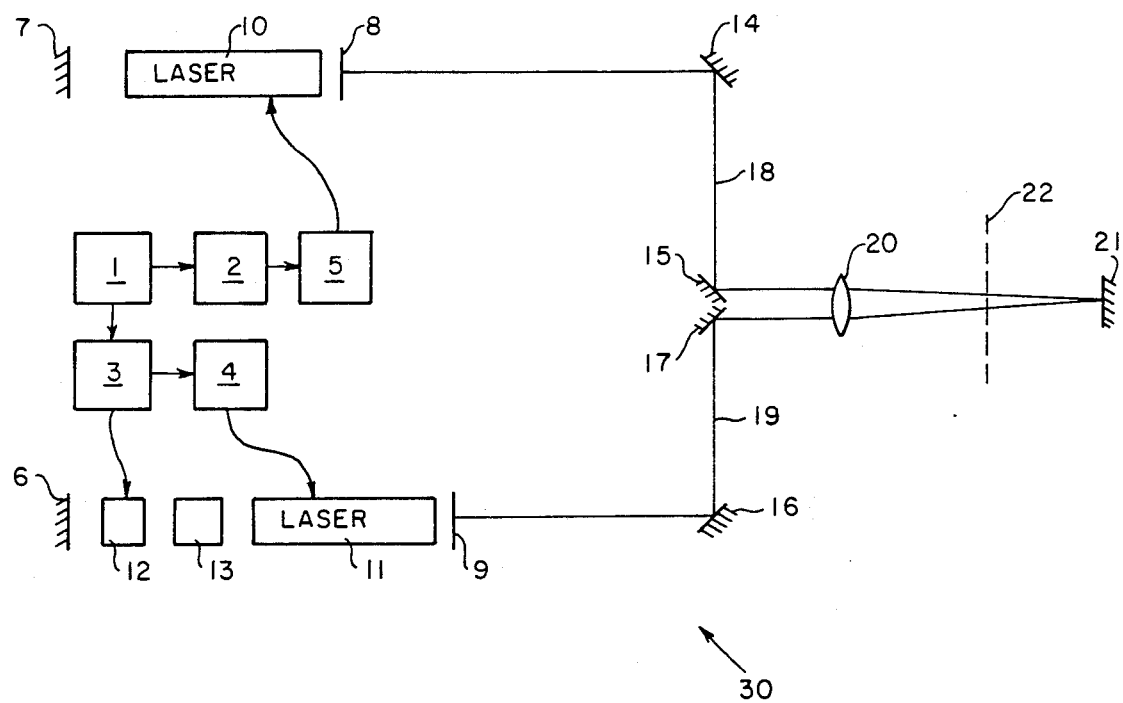
FIG. 1 is a block diagram of one embodiment of the present invention employing a Q-switched and a free-running laser system.

Continuing with FIG. 1, laser 10 is controlled by a master electronic timing circuit 1 that provides an output signal to a delay pulse generator 2 which in turn activates the high voltage power supply 5 to fire the flashlamps in the laser cavity. Simultaneously, the master electronic timing circuit 1 outputs a signal to a dual delay pulse generator 3 which provides two controllable trigger pulses to activate and operate the second laser in a Q-switched mode.

A second laser output beam 19 is produced by a second laser cavity 11, a rear cavity reflector 6, a front partial cavity reflector 9, with a beam polarizer and electro-optic cell (Pockels cell) 12. Signals from the dual delay pulse generator 3 provides signals to the high voltage power supply 4 to activate the flash lamps in the cavity and to the electro-optic cell 12 to operate laser 11 in a Q-switched mode. A polarizer 13 is employed between laser 11 and optic cell 12 as shown in FIG. 1.

The resultant output beam 19 is reflected by mirrors 16 and 17 to focusing lens 20, which brings the output beam 19 to a focus at the surface of the target 21. Operation of the laser cutting device 30 illustrated in FIG. 1 now provides that the free-running laser 10 is activated to provide free-running output 18 focused by optical lens 20 onto the surface of target 21 to create partial melting of the material comprising target 21. Just prior to the termination of pulse 18, Q-switched laser 11 produces output beam 19 which is a high peak power, a very short pulse which is also focused by lens 20 onto target 21. Lens 20 is positioned within system 30 so that both output beams 18 and 19 are superimposed upon the same spot of target 21. The short high power pulse 19 reaches target 21 after output beam 18 has melted or partially melted the target material. The high power Q-switched output 19 produces rapid vaporization of some of the molten target material yielding what has been referred to as a laser detonation wave (LSD) into the target material.

In simple words, the first laser 10 creates an essentially C-W output 18 which creates a melt on target 21. The second laser 11 then produces a high-energy short-duration pulse 19 which blows away the molten material. Test results show a dramatic improvement in the art for laser drilling efficiency and provides a stand-off target capability for heavy targets heretofore unknown within the art.

The timing and duration of the laser pulses will vary with application, but testing by applicants indicate the first laser pulse is best within the 400 to 600 microsecond range. Pulses of 520 microseconds were considered the best duration for the system and target parameters tested by applicants. The second Q-switched pulse was markedly shorter with 35 nanoseconds appearing to be a good duration.

The two-laser system of FIG. 1 is not restricted to Nd:YAG lasers or to laser 10 and 11 being the same type. Target parameters and distance will dictate system parts and it may be that two different laser pulses would improve drilling or provide better control of material removal. It is also considered to be within the disclosed invention to vary the timing of one or both outputs and in some circumstances to employ a series of Q-switched pulses as output 19.

The high efficiency drilling and cutting apparatus is adaptable to many fixed mounted applications where laser drilling and cutting are performed. Assembly lines where multiple drilling operations are to be performed on a stationary target can be assembled by one skilled in laser art using off-the-shelf parts. The system of FIG. 1 can be modified and the system made lighter and more portable by using a single power supply and delay pulse generator.

Figure 2:
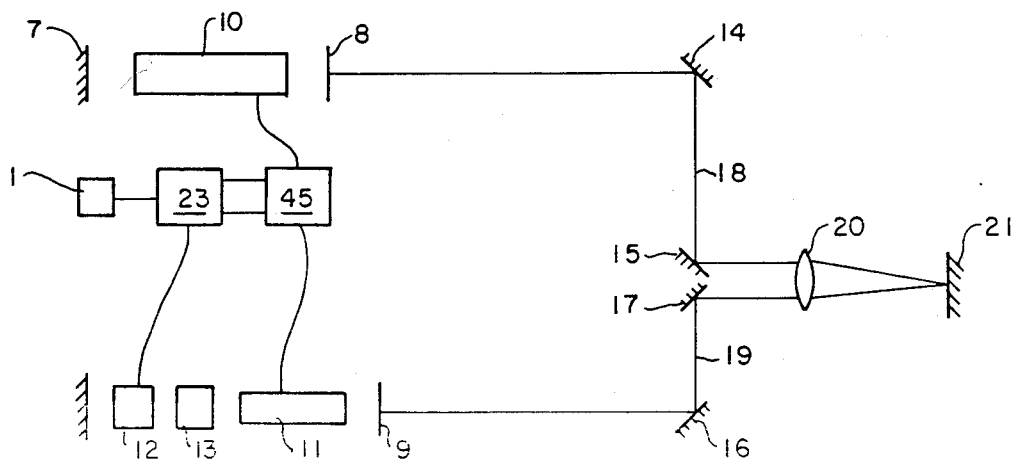
FIG. 2 is a block diagram of an embodiment wherein a Q-switched laser cavity and a free-running laser cavity share a single power supply and pulse generator.

Turning to FIG. 2, a more portable embodiment of the disclosed invention is illustrated wherein a master electronic timer 1 provides an output to a three-output pulse generator 23 which generates one pulse to fire each laser 10 and 11 and a third pulse to electro-optic cell 12 to activate the Q-switch function of laser 11. This version eliminates one pulse generator and uses a single power supply which lightens the system and imparts a portable field-capable laser drilling and cutting apparatus that continues to have a stand-off cutting capability. Variations on this system allow field personnel to carry a portable laser cutting device into the field and to deactivate ordnance by cutting critical parts or fuses without personnel having to enter the zone of danger.

Figure 3:
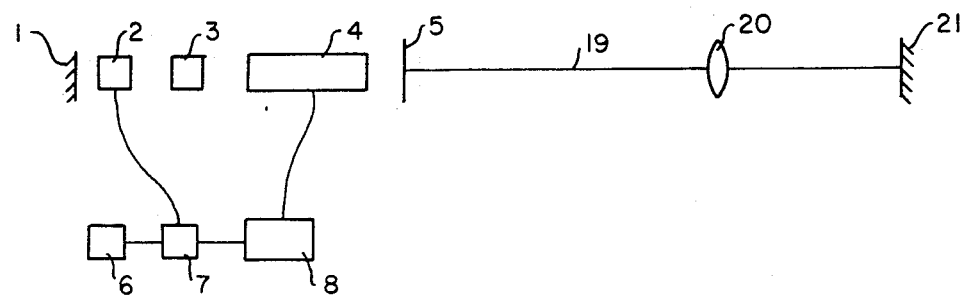
FIG. 3 is a block diagram of an embodiment using a single laser cavity alternatively operated between a free-running and a Q-switched mode.

FIG. 3 is a block diagram of one embodiment of the present disclosure which employs a single laser cavity 4 operated in both an essentially C-W mode and then in a Q-switched mode. In this system, master electronic timing circuit 6 provides a signal to a dual delay pulse generator 7 which first activates the flash lamp power supply 8 to fire the flash lamps in the laser cavity 4. Laser 4, now free-running, will output an essentially C-W beam. At a predetermined point in time, dual delay pulse generator 7 will send a signal to electro-optic cell 2 to block the polarized beam that has passed through polarizer 3. Once charged, a Q-switched high energy pulse will constitute beam 19 through the front partial reflecting mirror 5, focusing optics 20 and onto target surface 21.

Figure 4:
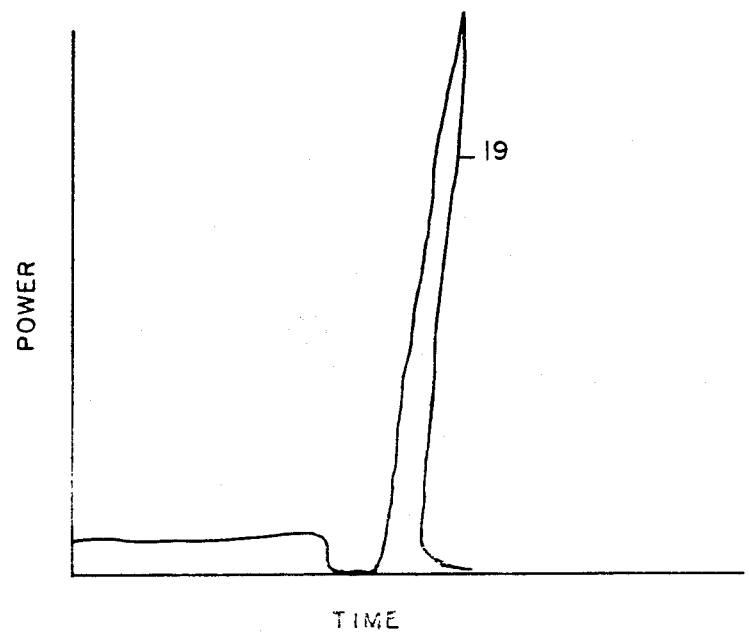
FIG. 4 is a drawing of the output waveform of FIG. 3.

FIG. 4 is a drawing of the output pulse 19 of the single laser cavity 4 of FIG. 3. In FIG. 4 output power is on the X axis and time on the Y axis. It can be clearly seen in FIG. 4 that output 19 is first a relatively long and low powered essentially C-W output to create a melt on the target, then output 19 is interrupted while the laser builds a charge that is then released as a high-power short duration spike to create the LSD described above.

The embodiment of FIG. 3 is the lightest and consequently the most portable embodiment of the invention illustrated herein. Because of the time required for the laser cavity to build up a high-peak power Q-switched pulse, output 19 has a period of low or no energy between the free-running low power pulse and the high-peak power energy Q-switched pulse. During this period the melt created on the target begins to cool and if it solidifies the Q-switched pulse will be inadequate to blow off the melt with a LSD. This manifests as a trade-off between system weight and drilling efficiency resulting in the most portable, i.e., lightest embodiment having a single laser cavity being restricted to targets requiring low drilling power.

Applicants built and tested their invention with many off-the-shelf parts known to those skilled in the laser art and easily adapted and adjusted to the various embodiments without undue experimentations. For example, the laser cavities used and tested by applicants were off-the-shelf Model FC-500 purchased from Kigre, Inc. In Hilton Head, SC. A model 600 laser cavity performs equally well s an alternate and is available from Control Laser, Inc. in Orlando, Fl.

The cavity reflectors 6, 7, 8 and 9 in FIGS. 1 and 2, along with numeral 1 and 5 in FIG. 3, were all off-the-shelf components procured from CVI Laser, Inc. in Alburquerque, NM. Laser Optics in Danbury, CT manufactures acceptable alternative components as do many other commercial supply sources known to technicians and engineers in the art. These same commercial suppliers provided the beam reflectors, and acceptable substitutes are widely available.

The focusing optic lenses were purchased commercially from Edmond Scientific in Barrington, NJ, and were Model Number P32,879. Again, many alternative commercial sources exist, such as CVI Laser, Inc. In Alburquerque, NM.

The pulse generators were Model 535, purchased commercially from Stanford Research Systems in Stanford, CA, but Precision Instruments, Model 9650, and Hewlett-Packard Model 8013B are both acceptable alternatives. The power supplies were commercial units purchased from Holobeam Laser, Inc., Model 600, available commercially from Orlando, Florida. Both Interstate Electronic Corp., Model HV285, out of New York, NY, and Hipotronics in Long Island, NY, provide acceptable commercial substitutes for the power supplies.

Finally, the electro-optic cells were Model 1058, available commercially from Lasermatric in Englewood, NJ, and the polarizers were Model MGTYB20, purchased commercially from Karl Lambrecht, Inc. in Chicago. Alternative commercial sources exist for the polarizers and electro-optic cells as they do for all commercial parts listed above.

The master electronic timing circuits were constructed locally by applicants, but acceptable commercial timing units are available and well known in the art. No special construction techniques were needed beyond those known to persons of average skill in the electronic arts.

Changes may be made in the construction and arrangement of parts or elements of the various embodiments as disclosed herein without departing from the spirit and scope of the invention as defined in the following claims.

What is claimed is:

1. A laser device for cutting or drilling a distant workpiece comprising:
   a first free running pulsed laser to create a partial melting of the distant workpiece; and
   a second Q-switched laser timed to create a laser detonation wave on the workpiece at the completion of the partial melt created by said first laser; and
   means for focusing said first and said second lasers on the distant workpiece.

2. A laser drilling device of claim 1 wherein said first and second lasers are chosen from the group of all lasers possible including doped crystals, glass or excimer, $CO_2$ and free electron devices.

3. A laser device according to claim 1 wherein said first and second lasers are Nd:YAG.

4. A laser drilling device of claim 3 wherein said first Nd:YAG laser produces a pulse of 400 to 600 microseconds.

5. A laser drilling device of 3 wherein said first Nd:YAG laser pulse is about 520 usec.

6. A stand-off laser drilling device comprising:
   a laser power supply including a capacitor; and
   two Nd:YAG laser heads, one free running and one Q-switched, triggered by said laser power supply; and
   means for focusing said two Nd:YAG laser heads whereby both laser beams are focused on the same target area.

7. A laser drilling device of claim 6 wherein said second Nd:YAG laser produces an approximate 35 ns pulse when Q-switched and an approximately 500 us pulse when free running.

8. A laser drilling device of claim 1 wherein said means for focusing is a beam splitter.

9. A laser drilling device of claim 7 wherein said means for focusing is a beam splitter.

10. A laser drilling device of claim 6 wherein said means for focusing said twin Nd:YAG laser heads is a beam splitter.

11. A laser drilling device of claim 2 wherein said means for focusing is a beam splitter.

12. A laser device for cutting or drilling a distant workpiece comprising:
    a single free running/Q-switched laser timed to first create a partial melt on the workpiece in a free running mode, then remove the partially melted material with a Q-switched pulse; and
    means for focusing said single laser on the distant workpiece.

13. A laser device according to claim 12 wherein said single laser is a Nd:YAG.

* * * * *